(12) United States Patent
Boucher et al.

(10) Patent No.: US 11,666,251 B2
(45) Date of Patent: Jun. 6, 2023

(54) SIGNAL AND TORQUE TRANSMITTING TORQUE COIL

(71) Applicant: HERAEUS DEUTSCHLAND GMBH & CO. KG, Hanau (DE)

(72) Inventors: Colin Boucher, St. Paul, MN (US); Shawn D. Bluhm, Lindstrom, MN (US); Stefan Schibli, Rodenbach (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 540 days.

(21) Appl. No.: 16/346,321

(22) PCT Filed: Oct. 31, 2016

(86) PCT No.: PCT/US2016/059756
§ 371 (c)(1),
(2) Date: Apr. 30, 2019

(87) PCT Pub. No.: WO2017/087149
PCT Pub. Date: May 26, 2017

(65) Prior Publication Data
US 2020/0037931 A1    Feb. 6, 2020

(51) Int. Cl.
A61B 5/145    (2006.01)
A61B 5/0215   (2006.01)
(Continued)

(52) U.S. Cl.
CPC .......... *A61B 5/145* (2013.01); *A61B 5/02154* (2013.01); *A61B 5/6851* (2013.01);
(Continued)

(58) Field of Classification Search
CPC .............. A61B 5/6851; A61B 5/02154; A61B 2034/2061; A61M 25/09; A61M 25/0102;
(Continued)

(56) References Cited

U.S. PATENT DOCUMENTS

| | | | |
|---|---|---|---|
| 5,060,660 A | 10/1991 | Gambale et al. |
| 5,103,543 A | 4/1992 | Hodgson |

(Continued)

FOREIGN PATENT DOCUMENTS

| | | |
|---|---|---|
| EP | 0661072 | 7/1995 |
| WO | 0040293 | 7/2000 |

(Continued)

*Primary Examiner* — Sean P Dougherty
(74) *Attorney, Agent, or Firm* — Dicke, Billig & Czaja, PLLC

(57) ABSTRACT

A torque coil 10 includes a first filar configured in an inner layer 14 that is helically wound in a constricted state such that it defines an inner lumen providing access between a proximal and distal end of the torque coil. A second filar is configured in an outer layer 18 that is helically wound over the inner layer in a constricted state. At least one of the first and second filars includes a signal transmitting material surrounded by an isolating material thereby allowing transmission of signals between the proximal and distal end of the torque coil in one of the layers. At least one of the first and (Continued)

Figure 1:
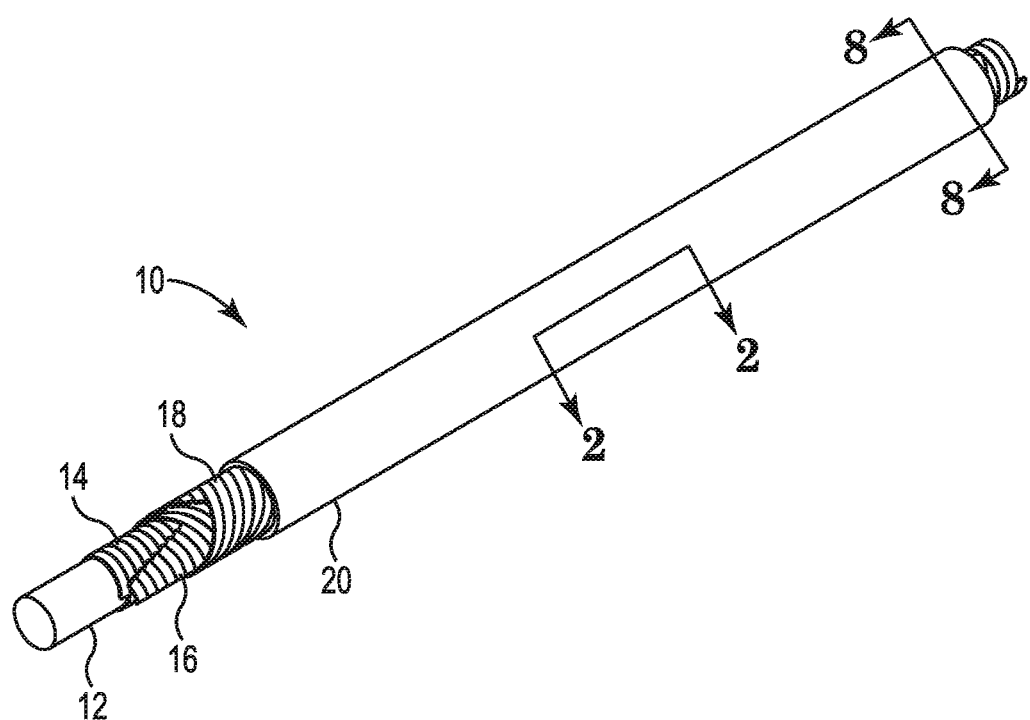

second filars includes a torque transmitting material thereby configuring the torque coil to transfer torque from the proximal to the distal end.

16 Claims, 8 Drawing Sheets

(51) Int. Cl.
*A61B 5/00* (2006.01)
*A61M 25/09* (2006.01)
*H01F 27/28* (2006.01)
*G02B 6/44* (2006.01)

(52) U.S. Cl.
CPC ............ *A61M 25/09* (2013.01); *H01F 27/28* (2013.01); *A61M 2025/09091* (2013.01); *G02B 6/4415* (2013.01)

(58) Field of Classification Search
CPC A61M 2025/09091; H01F 27/28; H01F 5/00; G02B 6/4415
See application file for complete search history.

(56) References Cited

U.S. PATENT DOCUMENTS

| | | |
|---|---|---|
| 5,836,946 A | 11/1998 | Diaz et al. |
| 6,191,414 B1 | 2/2001 | Ogle et al. |
| 6,210,395 B1 | 4/2001 | Fleischhacker et al. |
| 6,685,696 B2 | 2/2004 | Fleischhacker et al. |
| 6,978,185 B2 | 12/2005 | Osypka |
| 8,798,767 B2 | 8/2014 | Foster et al. |
| 2002/0183820 A1 | 12/2002 | Schell |
| 2007/0083132 A1 | 4/2007 | Sharrow |
| 2010/0093448 A1 | 4/2010 | Markham |
| 2012/0016451 A1 | 1/2012 | Struve et al. |
| 2013/0317372 A1 | 11/2013 | Eberle et al. |
| 2014/0336637 A1 | 11/2014 | Agrawal et al. |

FOREIGN PATENT DOCUMENTS

| | | |
|---|---|---|
| WO | 0198743 | 12/2001 |
| WO | 2009073913 | 6/2009 |
| WO | 2014025402 | 2/2014 |
| WO | 2016070099 | 5/2016 |

SIGNAL AND TORQUE TRANSMITTING TORQUE COIL

CROSS REFERENCE TO RELATED APPLICATIONS

This Utility Patent Application claims priority under 35 U.S.C. § 371 to International Application Serial No. PCT/US2016/059756, filed Oct. 31, 2016; which is incorporated herein by reference.

BACKGROUND

One embodiment relates to a helically-wound torque coil configured with signal and torque transmission and related method. In one embodiment, a coil includes a wire that is tightly wound over itself to form a multi-layer coil with a hollow lumen. In some instances, the torque coil can effectively transmit torque with the multi-layer coil arrangement, which is useful in many intervascular applications. Any signal transmission within the torque coil is, however, typically facilitated within the hollow lumen. Because the space within the lumen is limited and often needed for other functions, there is a need for the invention.

BRIEF DESCRIPTION OF THE DRAWINGS

FIG. 1 illustrates a partial cut-away perspective view of a torque coil in accordance with one embodiment.

FIG. 2 illustrates a perspective view of a cross-sectional portion of the torque coil in FIG. 1 in accordance with one embodiment.

FIG. 3A illustrates a cross-sectional portion of a torque coil in accordance with one embodiment.

FIG. 3B illustrate an enlarged view of the cross-sectional portion of the torque coil in FIG. 3A in accordance with one embodiment.

FIG. 4A illustrates a cross-sectional portion of a torque coil in accordance with one embodiment.

FIG. 4B illustrate an enlarged view of the cross-sectional portion of the torque coil in FIG. 4A in accordance with one embodiment.

FIG. 5A illustrates a cross-sectional portion of a torque coil in accordance with one embodiment.

FIG. 5B illustrate an enlarged view of the cross-sectional portion of the torque coil in FIG. 5A in accordance with one embodiment.

FIG. 6A illustrates a cross-sectional portion of a torque coil in accordance with one embodiment.

FIG. 6B illustrate an enlarged view of the cross-sectional portion of the torque coil in FIG. 6A in accordance with one embodiment.

FIG. 7 illustrates a partially assembled torque coil in accordance with one embodiment.

FIG. 8 illustrates an end view of a portion of a torque coil in accordance with one embodiment.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the invention can be positioned in a number of different orientations, the directional terminology is used for purposes of illustration and is in no way limiting. It is to be understood that other embodiments may be utilized and structural or logical changes may be made without departing from the scope of the invention. The following detailed description, therefore, is not to be taken in a limiting sense, and the scope of the invention is defined by the appended claims.

In one embodiment, a torque coil comprises a first filar configured in an inner layer that is helically wound in a constricted state such that it defines an inner lumen providing access between a proximal and distal end of the torque coil. A second filar is configured in an outer layer that is helically wound over the inner layer in a constricted state. At least one of the first and second filars comprises a signal transmitting material surrounded by an isolating material thereby allowing transmission of signals between the proximal and distal end of the torque coil in one of the layers. At least one of the first and second filars comprises a torque transmitting material thereby configuring the torque coil to transfer torque from the proximal to the distal end.

In one embodiment, with the torque coil previously described, at least one of the first and second filars comprises a metal wire covered with a polymer cover surrounding the metal wire.

In one embodiment, with any of the torque coils previously described, at least one of the first and second filars comprises an optical fiber core covered with a cladding surrounding the core.

In one embodiment, with any of the torque coils previously described, the torque coil is configured with at least one of at least one-to-one torque transfer, at least one-to-two torque transfer, and at least one-to-three torque transfer.

In one embodiment, any of the torque coils previously described further comprises a third filar configured in an intermediate layer between the inner and outer layers that is helically wound over the inner layer in a constricted state.

In one embodiment, with any of the torque coils previously described, at least two of the first, second and third filars comprise a metal wire covered with a polymer cover surrounding the metal wire thereby electrically isolating the metal wire such that at least two of the first, second and third filars transmits electrical signals between the proximal and distal end of the torque coil.

In one embodiment, with any of the torque coils previously described, each of the first, second and third filars comprise a metal wire covered with a polymer cover surrounding the metal wire thereby electrically isolating the metal wire such each of the first, second and third filars transmits electrical signals between the proximal and distal end of the torque coil.

In one embodiment, with any of the torque coils previously described, at least one of the first, second and third filars comprise a stiffening wire filar.

In one embodiment, with any of the torque coils previously described, at least two of the first, second and third filars comprise a stiffening wire filar.

In one embodiment, a torque coil comprises an inner layer comprising a first filar helically wound in a constricted state such that it defines an inner lumen providing access between a proximal and distal end of the torque coil. An intermediate layer comprises a second filar helically wound over the inner layer in a constricted state and an outer layer comprising a third filar helically wound over the intermediate layer in a constricted state. At least one of the first, second and third filars comprises a signal transmitting material surrounded by an isolating material thereby allowing transmission of signals between the proximal and distal end of the torque coil. At least one of the first, second and third filars comprises a torque transmitting material thereby configuring the torque coil to transfer torque from the proximal to the distal end.

In one embodiment, with any of the torque coils previously described, at least one of the first, second and third filars comprises a metal wire covered with a polymer cover surrounding the metal wire.

In one embodiment, with any of the torque coils previously described, at least one of the first, second and third filars comprises an optical fiber core covered with a cladding surrounding the core.

In one embodiment, with any of the torque coils previously described, the torque coil is configured with at least one of at least one-to-one torque transfer, at least one-to-two torque transfer, and at least one-to-three torque transfer.

In one embodiment, with any of the torque coils previously described, at least two of the layers comprise a metal wire filar covered with a polymer cover surrounding the metal wire filar thereby electrically isolating the metal wire filar such that electrical signals are transmitted between the proximal and distal end of the torque coil in at least two of the layers of the torque coil.

In one embodiment, with any of the torque coils previously described, each of the layers comprise a metal wire filar covered with a polymer cover surrounding the metal wire thereby electrically isolating the metal wire such that electrical signals are transmitted between the proximal and distal end of the torque coil in each of the layers of the torque coil.

In one embodiment, with any of the torque coils previously described, at least one layer comprises a stiffening wire filar.

In one embodiment, with any of the torque coils previously described, at least two layers comprise a stiffening wire filar.

The term "torque coil" may be understood as a tube made of at least one wound wire defining an inner lumen. The torque coil thereby forms a flexible tube for torque transmission, torque response and/or torque control. The torque coil may be flexible enough to be guided through blood vessels or body lumens and may be stiff enough to be pushed also through complex anatomies and e.g. calcified lesions without buckling.

A wound wire layer may be understood as a wire wound to form a tube. The wire may be helically wound. The wire may be wound in a constricted state, and thereby, provide the torque coil with stored energy. Here, the torque coil is made of at least two wound wire layers. The inner wire layer and the outer wire layer can be wound in the left or right hand direction. Torque is transferred best in the direction opposite of the wind direction.

FIG. 1 illustrates a partial cut-away perspective view of a helically-wound torque coil 10 in accordance with one embodiment. In one embodiment, torque coil 10 includes an inner layer 14, which in one embodiment is helically wound over mandrel 12. Torque coil 10 also includes an intermediate layer 16 helically wound over inner layer 14 (in the figure, a portion of intermediate layer 16 is cut away to show inner layer 14 below it). Torque coil 10 further includes an outer layer 18 helically wound over intermediate layer 16 (in the figure, a portion of outer layer 18 is cut away to show intermediate layer 16 below it).

In one embodiment, outer polymer cover 20 is formed over the combination of inner layer 14, intermediate layer 16, and outer layer 18, thereby securing the combination together. Because outer polymer cover is configured to sufficiently constrain the layers below it in some embodiments, once outer polymer cover 20 is in place, mandrel 12 can be removed, thereby opening an inner lumen 11 within torque coil 10. Such inner lumen 11 can be filled or used in various applications, as discussed below.

In one embodiment, inner layer 14 is tightly wound in a constricted state over mandrel 12, and each subsequent layer, that is, intermediate layer 16, outer layer 18, etc., is tightly wound in a constricted state over the previous layer across the entire layer. In one embodiment, a single wire filar is used for each of inner, intermediate and outer layers 14, 16 and 18 without ever being cut or interrupted. In this way, inner layer 14 is wound on mandrel 12, and then intermediate layer 16 is wound back over inner layer 14 without ever cutting the wire that is used to wind the layers. The same can be done for outer layer 18 and for any additional intermediate layers.

In one embodiment, a single wire filar is used, but is broken or cut between each adjacent layer. But, because each layer is tightly wound in a constricted state, each immediately adjacent over layer, that is, the layer subsequently wound over the previous layer, constrains the previous layer and prevents its unwinding. Outer layer 18 in the embodiment of FIG. 1 can be constrained by outer polymer cover 20, or by other means, as is discussed further below.

Because all layers are constrained, there is no slippage between the layers. In this way torque coil 10 has excellent torque transmission characteristics. For example, in one embodiment torque coil 10 has "one-to-one" torque, that is, a single full rotation at one end of torque coil 10 results in a single full rotation at the opposite end. In other embodiments, torque coil 10 has good torque transmission characteristics, for example, where it has "two-to-one" torque, that is, two full rotations at one end of torque coil 10 results in a single full rotation at the opposite end. In yet other embodiments, torque coil 10 has acceptable torque transmission characteristics, for example, where it has "three-to-one" torque, that is, three full rotations at one end of torque coil 10 results in a single full rotation at the opposite end.

Although the illustrated embodiment in FIG. 1 has three layers (14, 16, 18) within outer polymer cover 20, using just two layers (for example, inner layer 14 and outer layer 18), or using more than three layers, are also possible for torque coil 10 by adding multiple additional intermediate layers.

In the example illustrated in FIG. 1, inner layer 14 is illustrated as helically wound with a pitch in a first direction, while intermediate layer 16 is helically wound with a pitch in a second direction that is reverse relative to the first direction. Outer layer 18 is then illustrated as helically wound with a pitch substantially in the first direction, similar to inner layer 14. Reverse winding in this way allows torque coil 10 to be used in rotating applications without collapsing in or winding open with the rotation of torque coil 10. Reverse winding provides additional stability to torque coil 10 for bi-directional rotational applications, such that it can be rotated in both clockwise and counterclockwise directions without collapsing in or winding open with the rotation.

Such an embodiment may be useful in various rotational intravascular applications. Furthermore, torque coil 10 is extremely resistant to kinking and resistant to elongation and has excellent compression resistance between adjacent filars, such that it may be useful in intravascular applications requiring pushing, pulling and bending of torque coil 10. Despite these strengths and excellent bi-directional turning, torque coil 10 also has excellent flexibility.

In one embodiment, at least one of inner layer 14, intermediate layer 16 and outer layer 18 is configured for signal transmission. As such, in addition to providing excellent torque characteristics, torque coil 10 is also configured to transmit signals from one of its ends to its opposite end through one of its layers. Accordingly, the layers of torque coil 10 provide both a good structural support for excellent torque transmission as well as a signal transmission function.

Figure 2:
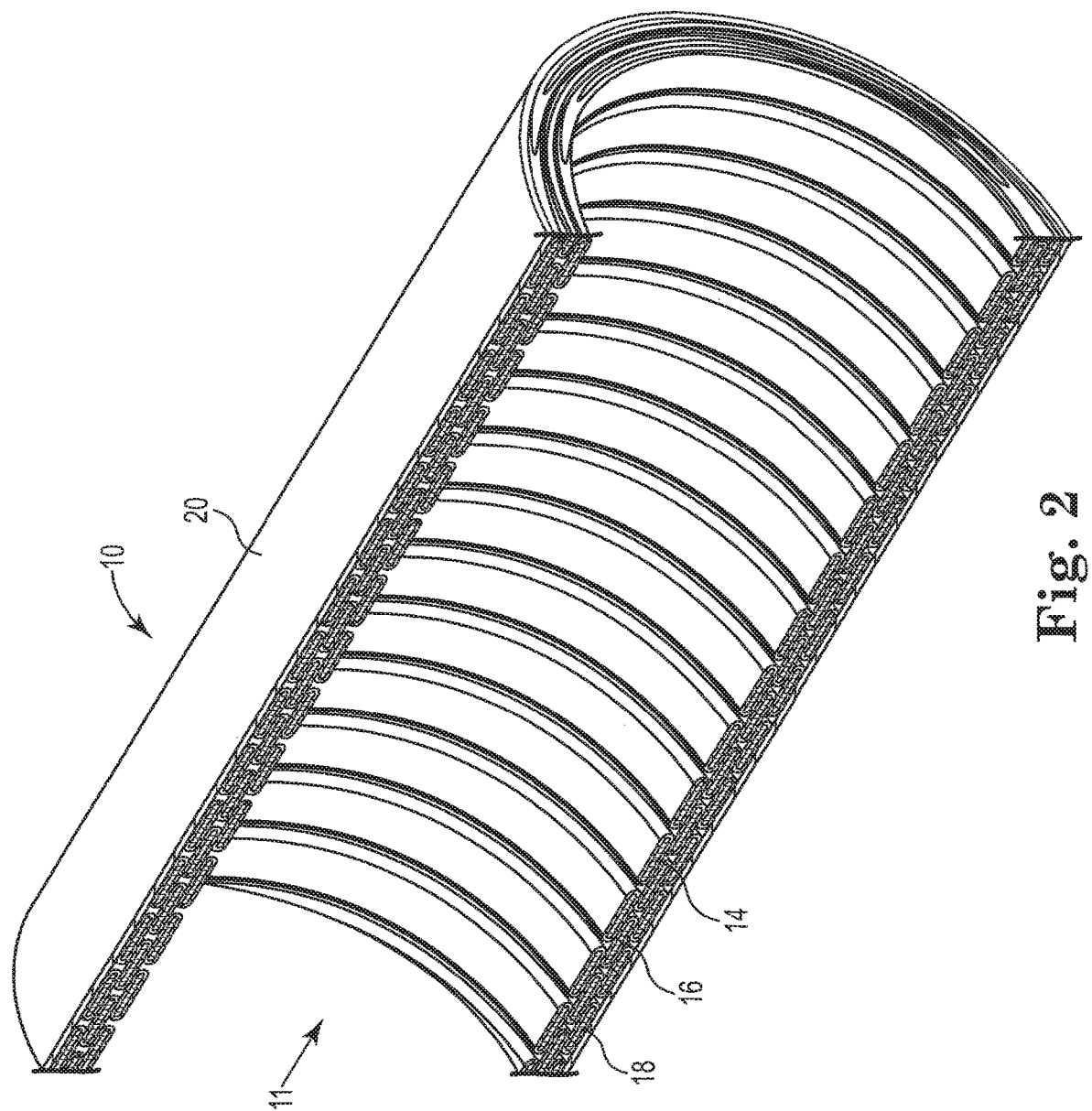

In one embodiment, wire filars used in one of more of inner layer 14, intermediate layer 16 and outer layer 18 include a metal wire core surrounded by an insulative coating. FIG. 2 illustrates a sectional view of layers 14, 16, 18 secured within outer polymer cover 20. In one embodiment, each wire stand that is used within each layer, has its own coating.

Furthermore, torque coil 10 also provides inner lumen 11, which provides a relatively large access that is quite useful in many applications. When torque coil 10 is used in any of a variety of rotational intravascular applications, inner lumen 11 can provide access from the proximal to the distal end of the coil for aspiration of fluid, delivery of fluid or access for additional guides, wires and instruments. Because both the torque transmission and signal transmission functions are provided in the inner layer 14, intermediate layer 16 or outer layer 18, inner lumen 11 is left open to provide this additional access important in many intervascular applications.

Figure 3A:
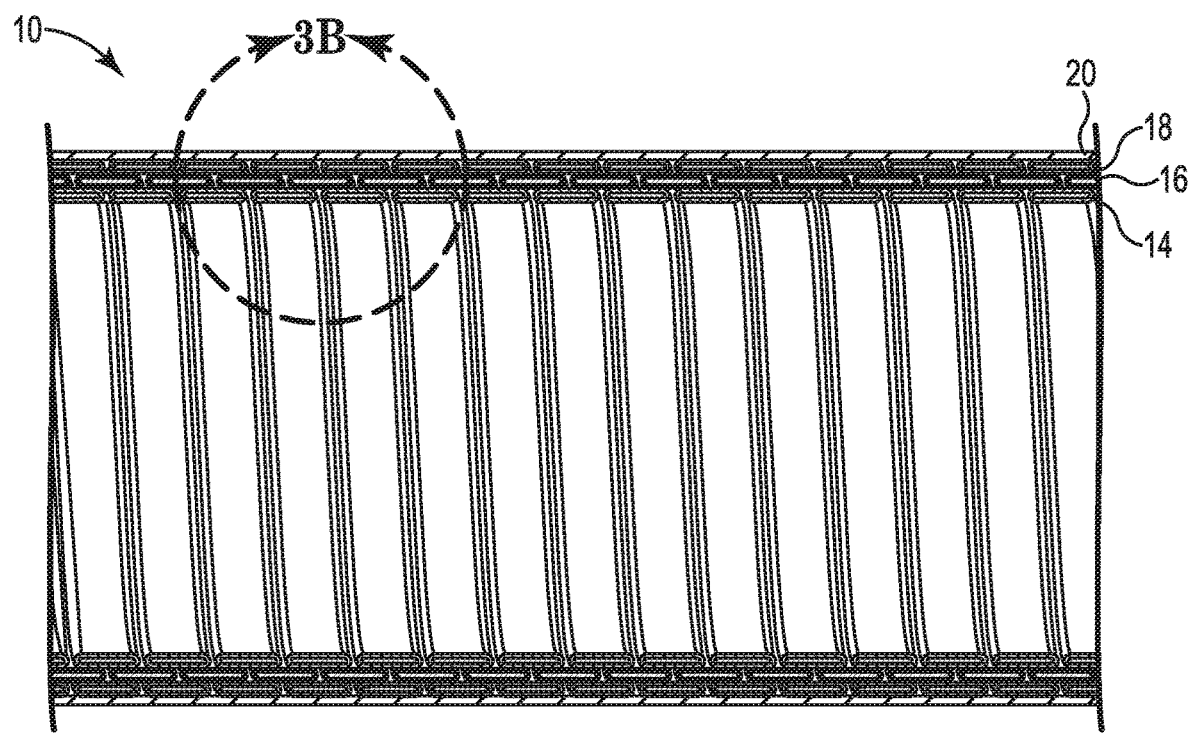
Figure 3B:
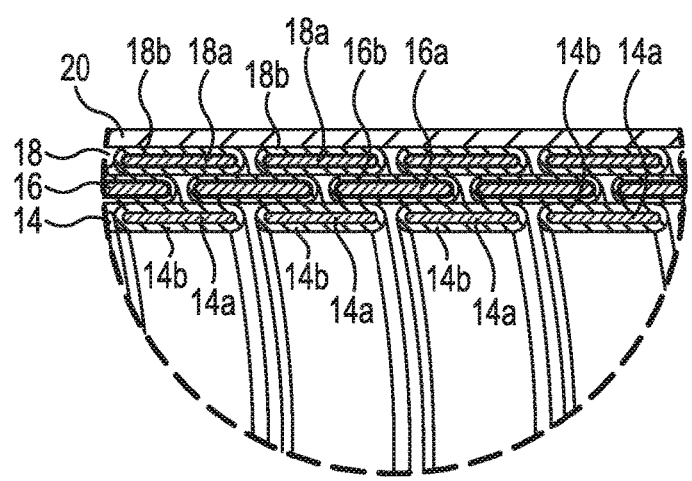

FIG. 3A illustrates a cross-sectional view, and FIG. 3B illustrates an enlarged detailed view of section 3B shown in dotted lines in FIG. 3A. In one embodiment, each of layers 14, 16 and 18 are tightly wound over a preceding layer, that is, the wire filar used to wind intermediate layer 16 is helically wound tightly over inner layer 14 (which is wound over a mandrel) and the wire filar used in outer layer 18 is helically wound tightly over intermediate layer 16.

In one embodiment, inner layer 14 includes a wire filar that has a wire core 14a surrounded by an insulative coating 14b. Similarly, intermediate layer 16 and outer layer 18 respectively include a wire filar that has a wire core 16a, 18a surrounded by an insulative coating 16b, 18b. Accordingly, each wire core 14a, 16a, 18a within each filar of each layer 14, 16, 18 is electrically isolated from each adjacent wire core by insulative coating 14b, 16b, 18b. In this way, a signal can be transmitted independently along each of wire core 14a, 16a, 18a in each layer 14, 16, 18. Furthermore, because each of layers 14, 16 and 18 are tightly wound over a preceding layer, torque coil 10 also had excellent torque transmission characteristics. In the embodiment illustrated in FIG. 3, the wire core 14a, 16a, 18a is flat or rectangular, but other shapes can be used in accordance with other embodiments.

In some embodiments, the wire used in wire core 14a, 16a, 18a is made from one or more of stainless steel, Nitinol®, MP35N, titanium and tantalum. Also, in various embodiments insulative coating 14b, 16b, 18b is made from one or more of pebax, nylon, PET, FEP, polyurethane, polyimide, PTFE, HDPE, and PEEK. Also, various combinations can be used. For example, wire used for wire core 14a can be different than that used for wire core 16a and/or 18a. Furthermore, multiple filars can be used in any of layers 14, 16, 18 such that wire materials for the wire core can vary within any particular layer. The same is true for the insulative coating, which can vary in the different layers or even within a layer using different filars.

In some embodiments, each filar of each layer 14, 16, 18 has a wire core 14a, 16a, 18a of sufficient diameter and rigidity so as to ensure good torque transmission characteristics for torque coil 10, as well as the signal transmission properties. In some embodiments, however, the wire core used in a filar for one or more of the layers may be insufficient to provide adequate support for transmitting torque from one end of the torque coil to the other (that is, less than three-to-one). Also, the use of some electrically insulative materials for insulative coating 14b, 16b, 18b can add less rigid materials that degrade the torque transmission characteristics of the torque coil. In other words, when a full rotation is applied to one end of the torque coil, something less than a full rotation is achieved on the other end because of the lack of sufficient rigidity of the materials. In such embodiments, an additional structural or stiffening member can be used.

Figure 4A:
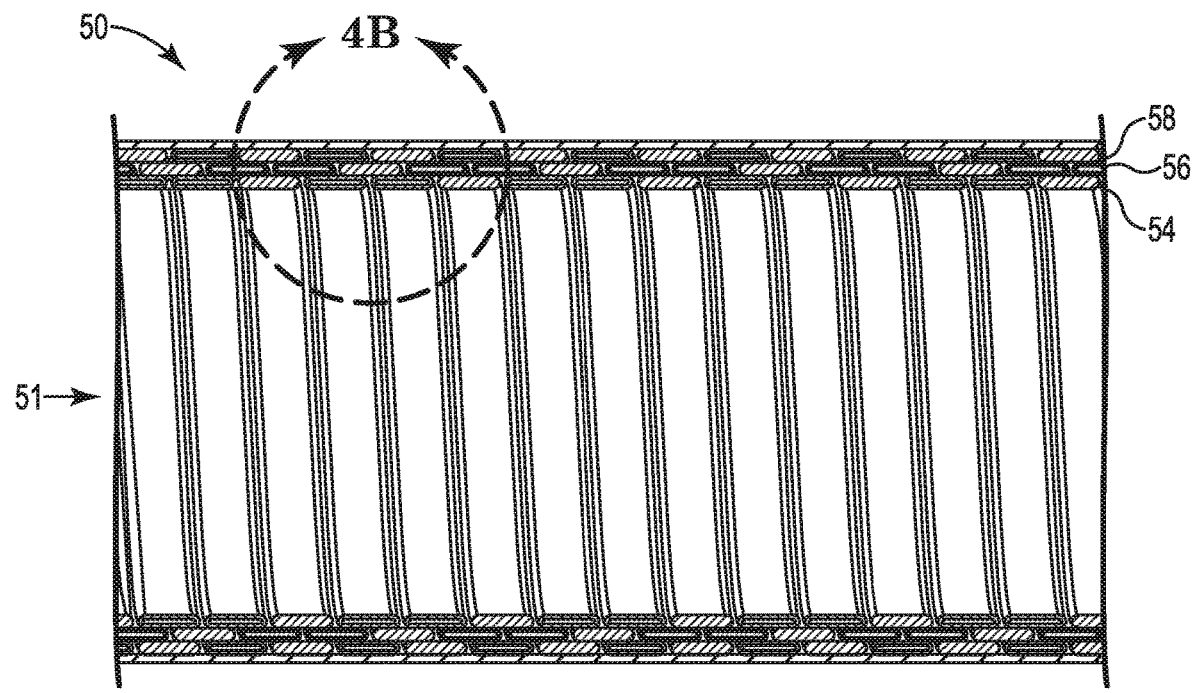
Figure 4B:
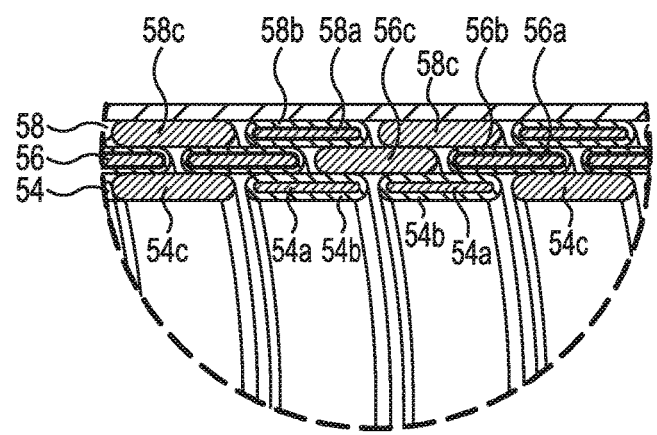

For example, FIGS. 4A and 4B illustrate cross-sectional and detailed views of a torque coil 50 in accordance with one embodiment. Similar to torque coil 10 above, in one embodiment torque coil 50 includes inner lumen 51, inner layer 54, intermediate layer 56 and outer layer 58, each layer tightly wound over a preceding layer or a mandrel, and at least some of the layers include a stiffening filar to increase rigidity and torque transfer.

In one embodiment, each of the inner, intermediate and outer layers 54, 56, 58 are "multi-filar layers," that is, each layer includes multiple filars tightly and helically wound at once. In one embodiment, inner layer 54, intermediate layer 56 and outer layer 58 respectively include a wire filar that have a wire core 54a, 56a, 58a surrounded by an insulative coating 54b, 56b, 58b. Furthermore, inner layer 54, intermediate layer 56 and outer layer 58 each respectively also include stiffening filars 54c, 56c, 58c, which in one embodiment are solid metal wires that provide additional structural support to each layer 54, 56, 58. In one embodiment, stiffening filars 54c, 56c, 58c are solid metal filars of stainless steel, Nitinol®, MP35N, titanium or tantalum.

Accordingly, the provision of additional stiffening filars 54c, 56c, 58c, in combination with wire cores 54a, 56a, 58a, ensures that torque coil 50 has at least adequate, and in some embodiments good or excellent, torque transmission characteristics. Furthermore, because each wire core 54a, 56a, 58a is electrically isolated from each adjacent wire core and each from each stiffening filar 54c, 56c, 58c in each layer by insulative coating 54b, 56b, 58b, a signal can be transmitted independently along each of wire core 54a, 56a, 58a. In addition, torque coil 50 also provides inner lumen 51, which provides a relatively large access between the proximal and distal ends of torque coil 50 that is quite useful in many intervascular applications. Although torque coil 50 is illustrated with stiffening filars 54c, 56c, 58c in each layer 54, 56, 58, in other embodiments stiffening filars can be used in only one or two of layers 54, 56, 58.

In one embodiment, one or more of fiber optic cables are used as filars in one or more of layers 54, 56, 58. For example, each of cores 54a, 56a, 58a can be optical cores, and each is respectively surrounded by a cladding 54b, 56b, 58b, such that optical signals can be transmitted within cores 54a, 56a, 58a, while being isolated from one another. Because fiber optic cables would have relatively poor torque transfer capability, however, the provision of stiffening filars 54c, 56c, 58c ensure that torque coil 50 still has good or excellent, torque transmission characteristics, in addition to the signal transmission provided in the fiber optic cores 54a, 56a, 58a.

FIGS. 5A-5B and 6A-6B respectively illustrate cross-sectional and detailed views of a torque coil 70 and 90 in accordance with various embodiments. Torque coils 70 and 90 each respectively include inner layer 74, 94 intermediate layer 76, 96 and outer layer 78, 98, each layer tightly wound over a preceding layer or a mandrel. Each respectively define inner lumens 71, 91.

Figure 5A:
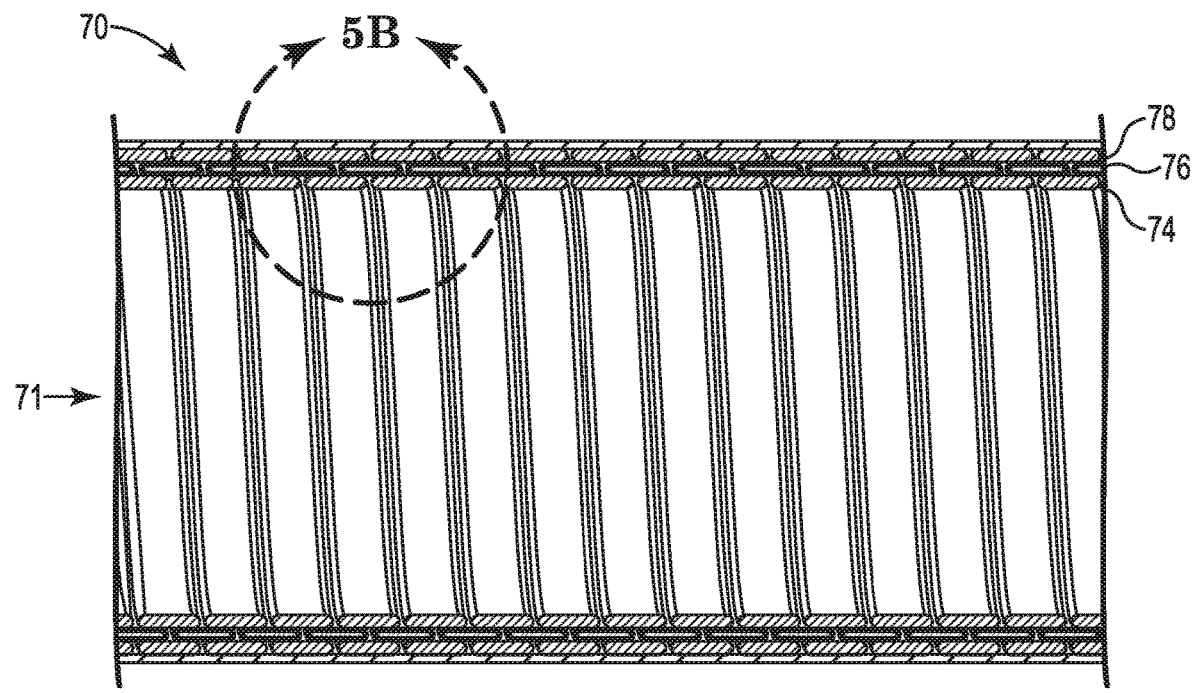
Figure 5B:
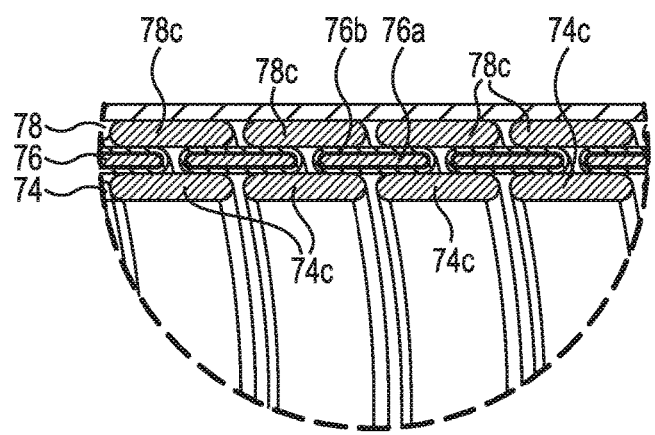

Torque coil 70 illustrated in FIGS. 5A-5B includes stiffening filar 74c in inner layer 74 and stiffening filar 78c in outer layer 78. Although neither stiffening filar is configured for signal transmission, each provides significant stiffening to torque coil 70 such that it provides excellent torque transmission characteristics. Similar to prior configurations, intermediate layer 76 is provided with a wire filar that has a wire core 74a surrounded by an insulative coating 74b. As such, signal transmission is readily enabled via wire core 74a. Consequently, torque coil 70 provides excellent torque transmission, signal transmission and provides an unobstructed inner lumen 71 useful for many intervascular procedures.

Figure 6A:
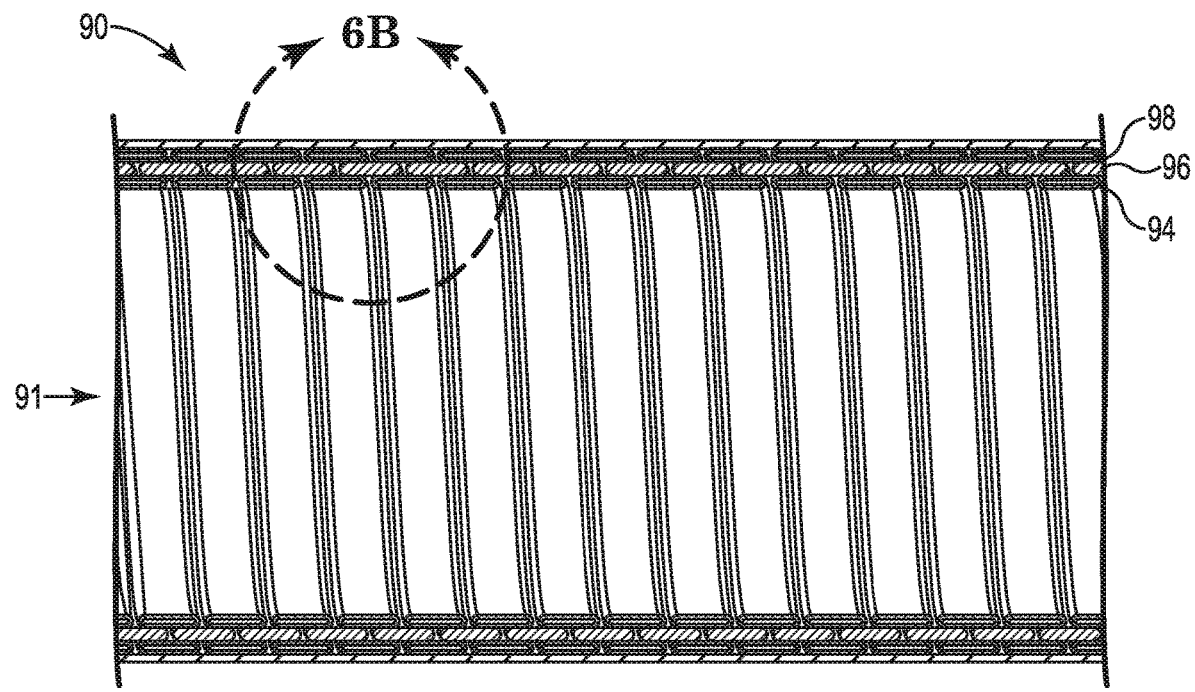
Figure 6B:
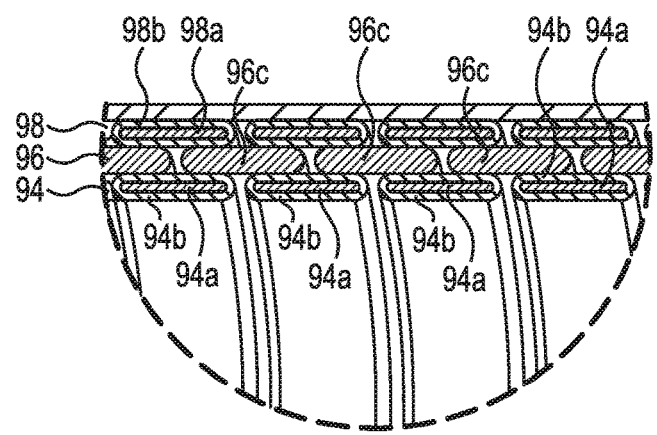

Torque coil 90 illustrated in FIGS. 6A-6B includes a stiffening filar 96c in intermediate layer 96. Although the stiffening filar is not configured for signal transmission, it provides significant stiffening to torque coil 90 such that it provides excellent torque transmission characteristics. Similar to prior configurations, inner layer 94 and outer layer 98 are respectively provided with a wire filar that has a wire core 94a, 98a surrounded by an insulative coating 94a, 98a. As such, signal transmission is readily enabled via wire cores 94a, 98a. Consequently, torque coil 90 provides excellent torque transmission, signal transmission and provides an unobstructed inner lumen 91 useful for many intervascular procedures. As with prior embodiments, fiber optic cores 76a and 94a, 98a may also be used for signal transmission.

In some embodiments, torque coils 10, 50, 70 and 90 are configured for very small applications, such as for the vascular system of humans and animals. In some examples, the wire used in each of the layers has a wire diameter (WD) as small as 0.0005 inches up to 0.004 inches. In some examples, the inner lumens 11, 51, 71 and 91 of torque coils 10, 50, 70 and 90 have an inner diameter (ID) as small as 0.008 inches up to 0.220 inches. In some examples, the outer diameter (OD) of torque coils 10, 50, 70 and 90 is 0.01 inches and 0.250 inches. Different OD and ID sizes for torque coils 10, 50, 70 and 90 are also possible where various different size wire is used.

Furthermore, the illustrations herein primarily show the wire that is used in the various layers of the torque coils as flat or rectangular, but other shapes can be used in accordance with other embodiments. For example, round wire or other shapes can be used.

The filars within the layers of the torque coils can be wound in variety of ways according to embodiments. In the embodiment illustrated in torque coil 10 of FIGS. 1-3, one convolution of wire is wound at one time for each of wire layers 14, 16 and 18. The embodiment of torque coil 50 illustrated in FIG. 5 is a multi-filar coil, where multiple convolutions of adjacent wire are wound at once in a layer. Two, three, four, five or more adjacent wire helices can be wound within each layer at one time.

Figure 7:
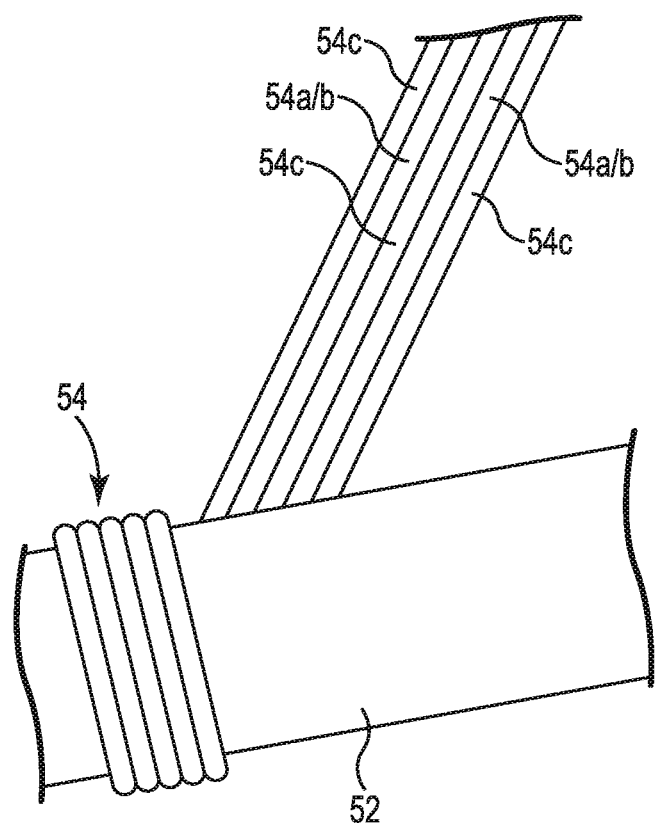

For example, FIG. 7 illustrates a partial assembly of a multi-filar layer 54 of torque coil 50 (illustrated as fully assembled in FIG. 5). In one embodiment, assembly of torque coil 50 begins with a first layer 54 being wound over a mandrel 52. In the example, first layer 54 is wound with five adjacent wire filars at one time. In one embodiment, the five adjacent wire filars consist of stiffening filars 54c alternating with an insulative coating 54b and wire core 54a combination. These five filars are wound in constricted state immediately adjacent each other until the first layer is complete. The second layer 56 is then wound directly over this first layer 54, and can be a single filar or another multi-filar layer.

Figure 8:
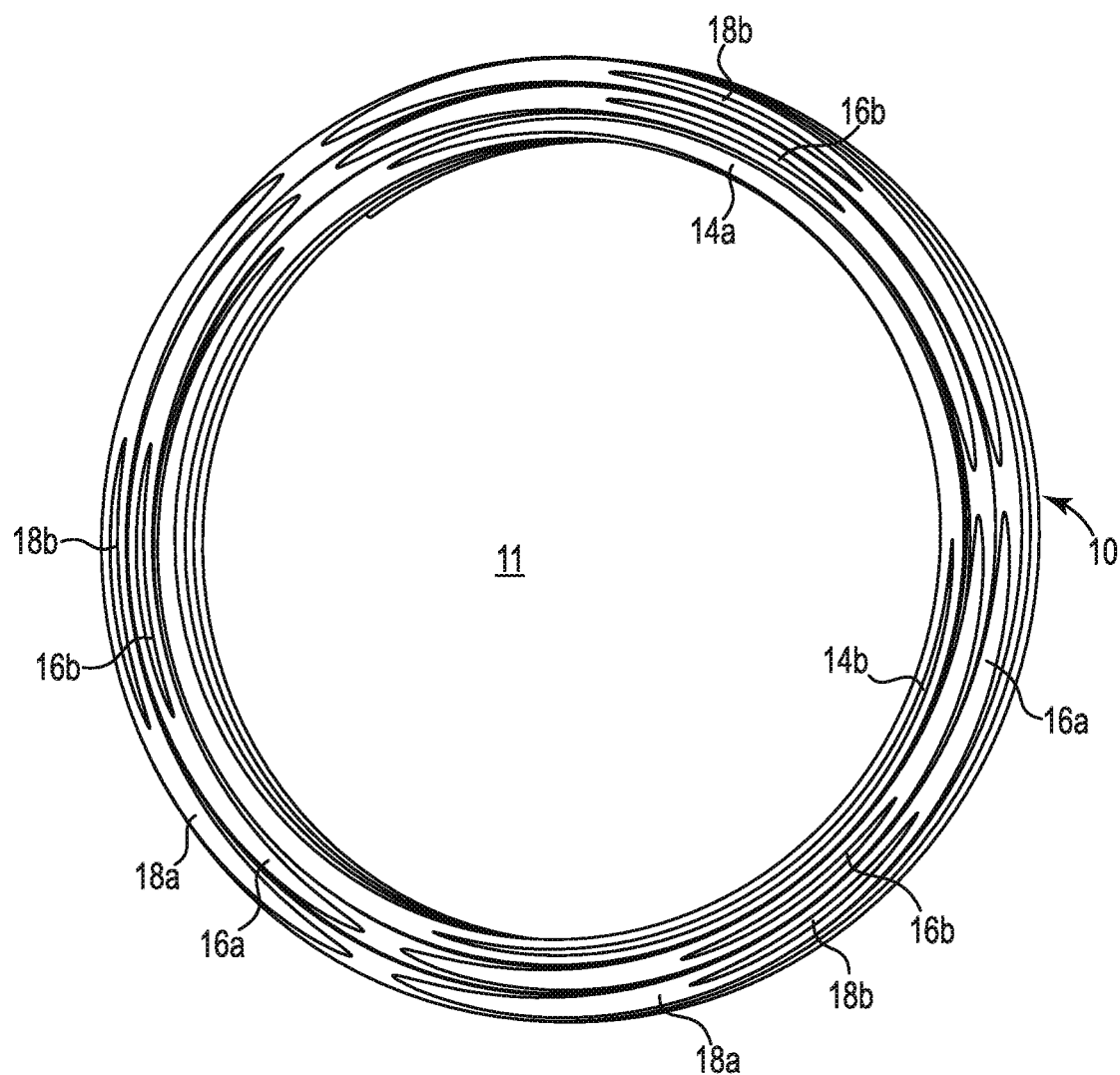

FIG. 8 illustrates an end view of a portion of a torque coil 10 in accordance with one embodiment. In the illustrated embodiment, torque coil 10 illustrated in FIGS. 1-3 has been heat treated at its ends in order to secure each of the layers 14, 16, 18 to each other. FIG. 8 illustrates a section view of one of the ends as taken along line 8-8 in FIG. 1. Any of torque coils 10, 50, 70 and 90 can be heat treated, such that any polymer coating from the insulative coating flows and combines with adjacent polymer material.

In FIG. 8, wire cores 14b, 16b, 18b are illustrated embedded in insulative coatings 14b, 16b, 18b after the heat treatment of the end portion of torque coil 10. Accordingly, the various layers 14, 16, 18 are bonded together once the polymer coatings re-solidify. In one embodiment, this allows the torque coil to avoid the use of an outer coating, such as outer coating 20 illustrated in FIG. 1.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof.

What is claimed is:

1. A torque coil comprising:
    a first filar configured in an inner layer that is helically wound in a constricted state such that the first filar defines an inner lumen providing access between a proximal and distal end of the torque coil;
    a second filar configured in an outer layer that is helically wound over the inner layer in a constricted state;
    a third filar configured in an intermediate layer between the inner and outer layers that is helically wound over the inner layer in a constricted state and such that the first and second filars are adjacent and directly contacting each other with no intervening layers, and such that the second and third filars are adjacent and directly contacting each other with no intervening layers;
    a stiffening wire filar in at least one of the inner, intermediate, and outer layers;
    at least one of the first, second, and third filars comprises a signal transmitting material coated by an isolating material, each filar having its own coating of the isolated material within its layer such that each filar is electrically isolated from the stiffening wire filar within the layer, thereby allowing transmission of signals between the proximal and distal end of the torque coil in one of the layers, and at least one of the first and second filars comprises a torque transmitting material thereby configuring the torque coil to transfer torque from the proximal to the distal end.

2. The torque coil of claim 1, wherein at least one of the first and second filars comprises a metal wire covered with a polymer cover surrounding the metal wire.

3. The torque coil of claim 1, wherein at least one of the first and second filars comprises an optical fiber core covered with a cladding surrounding the core.

4. The torque coil of claim 1, wherein the torque coil is configured with at least one of at least one-to-one torque transfer, at least one-to-two torque transfer, and at least one-to-three torque transfer.

5. The torque coil of claim 1, wherein the at least two of the first, second and third filars comprise a metal wire covered with a polymer cover surrounding the metal wire thereby electrically isolating the metal wire such that at least two of the first, second and third filars transmits electrical signals between the proximal and distal end of the torque coil.

6. The torque coil of claim 1, wherein each of the first, second and third filars comprise a metal wire covered with a polymer cover surrounding the metal wire thereby electrically isolating the metal wire such each of the first, second and third filars transmits electrical signals between the proximal and distal end of the torque coil.

7. The torque coil of claim 1, wherein the at least one of the first, second and third filars comprise a stiffening wire filar.

8. The torque coil of claim 1, wherein the at least two of the first, second and third filars comprise a stiffening wire filar.

9. A torque coil comprising:
   an inner layer comprising a first filar helically wound in a constricted state such that the first filar defines an inner lumen providing access between a proximal and distal end of the torque coil;
   an intermediate layer comprising a second filar helically wound directly over the inner layer in a constricted state such there is no layer between the inner and intermediate layers; and
   an outer layer comprising a third filar helically wound directly over the intermediate layer in a constricted state such there is no layer between the intermediate and outer layers; and
   at least one of the first, second and third filars comprises a signal transmitting material surrounded by an isolating material, each filar having its own coating of the isolated material within its layer, thereby allowing transmission of signals between the proximal and distal end of the torque coil, and at least one of the first, second and third filars comprises a torque transmitting material thereby configuring the torque coil to transfer torque from the proximal to the distal end, wherein the torque transmitting material and signal transmitting material are electrically isolated from each other by the coating of the isolated material within the layer.

10. The torque coil of claim 9, wherein at least one of the first, second and third filars comprises a metal wire covered with a polymer cover surrounding the metal wire.

11. The torque coil of claim 9, wherein at least one of the first, second and third filars comprises an optical fiber core covered with a cladding surrounding the core.

12. The torque coil of claim 9, wherein the torque coil is configured with at least one of at least one-to-one torque transfer, at least one-to-two torque transfer, and at least one-to-three torque transfer.

13. The torque coil of claim 9, wherein the at least two of the layers comprise a metal wire filar covered with a polymer cover surrounding the metal wire filar thereby electrically isolating the metal wire filar such that electrical signals are transmitted between the proximal and distal end of the torque coil in at least two of the layers of the torque coil.

14. The torque coil of claim 9, wherein each of the layers comprise a metal wire filar covered with a polymer cover surrounding the metal wire thereby electrically isolating the metal wire such that electrical signals are transmitted between the proximal and distal end of the torque coil in each of the layers of the torque coil.

15. The torque coil of claim 9, wherein the at least one layer comprises a stiffening wire filar.

16. The torque coil of claim 9, wherein at least two layers comprise a stiffening wire filar.

* * * * *